(12) United States Patent
Hechel et al.

(10) Patent No.: US 6,454,730 B1
(45) Date of Patent: Sep. 24, 2002

(54) THERMAL FILM ULTRASONIC DOSE INDICATOR

(75) Inventors: Dennis Hechel, Gurnee, IL (US); William Edleman, Sharon, MA (US); Gene Segalis, Deerfield, IL (US)

(73) Assignee: Misonix Incorporated, Farmingdale, NY (US)

( * ) Notice: Subject to any disclaimer, the term of this patent is extended or adjusted under 35 U.S.C. 154(b) by 0 days.

(21) Appl. No.: 09/285,559

(22) Filed: Apr. 2, 1999

(51) Int. Cl.$^7$ .................................................. A61H 1/00
(52) U.S. Cl. ........................... 601/2; 600/439; 600/549; 116/207; 601/3
(58) Field of Search ................................ 600/439, 549; 601/2–4; 604/22–24; 116/207

(56) References Cited

U.S. PATENT DOCUMENTS

| | | | |
|---|---|---|---|
| 4,030,482 A | * | 6/1977 | Navato |
| 4,070,912 A | * | 1/1978 | McNaughtan |
| 4,154,106 A | * | 5/1979 | Inoue et al. |
| 4,198,861 A | * | 4/1980 | Mung-Kuen Luk |
| 4,232,684 A | * | 11/1980 | Chervitz |
| 4,302,971 A | * | 12/1981 | Luk |
| 4,333,477 A | * | 6/1982 | Chervitz |
| 4,437,471 A | * | 3/1984 | Nelson |
| 4,509,533 A | * | 4/1985 | Chervitz |
| 4,889,122 A | * | 12/1989 | Watmough et al. |
| 5,230,334 A | * | 7/1993 | Klopotek |
| 5,291,890 A | * | 3/1994 | Cline |
| 5,573,921 A | * | 11/1996 | Behnke et al. |
| 5,618,275 A | * | 4/1997 | Bock |
| 5,776,074 A | * | 7/1998 | Marzorati |
| 5,873,892 A | * | 2/1999 | Cohen |
| 5,947,988 A | * | 9/1999 | Smith |
| 6,039,048 A | * | 3/2000 | Silberg |
| 6,050,943 A | * | 4/2000 | Slayton et al. |
| 6,067,371 A | * | 5/2000 | Gouge et al. |
| 6,071,239 A | * | 6/2000 | Cribbs et al. |
| 6,113,559 A | * | 9/2000 | Klopotek |
| 6,128,523 A | * | 10/2000 | Bechtold et al. |
| 6,135,968 A | * | 10/2000 | Brounstein |

\* cited by examiner

*Primary Examiner*—Marvin M. Lateef
*Assistant Examiner*—Runa Shah Qaderi
(74) *Attorney, Agent, or Firm*—Welsh & Katz, Ltd.

(57) ABSTRACT

A method and apparatus are provided for applying an ultrasound treatment to a portion of a human body. The method includes the steps of determining a temperature rise which the body portion will experience when a dosage limit of the ultrasound treatment has been reached. The method further includes the steps of disposing on the body portion an indicator adapted to provide a visual change at the determined temperature and applying ultrasound to the body portion until the indicator provides the visual change at the determined temperature.

18 Claims, 2 Drawing Sheets

THERMAL FILM ULTRASONIC DOSE INDICATOR

BACKGROUND OF THE INVENTION

1. Field of the Invention

The present invention relates to ultrasound and more particularly to ultrasound devices used for imaging, cutting or removal of tissue and/or matter from a living body.

2. Description of Related Art

Probes or scalpels for the fragmentation and removal of materials, tissue and fluids from living beings are known to the art. For example, U.S. Pat. No. 2,227,727, issued Jan. 7, 1941 to Vincent Leggiardro, discloses an apparatus for fragmenting naturally formed stones, such as kidney stones, and the like, utilizing a high speed reciprocating rod which may have a blunt end, a sharp or chisel point, a cutting blade, or combination thereof, such as a cutting blade having a blunt end.

A particular arrangement in an ultrasonically vibrated surgical tool using an irrigation fluid and an anti-coagulant is disclosed in U.S. Pat. No. 4,493,694, issued Jan. 15, 1985, to David G. Wuchinich, utilizes a hollow tool having a suction passage and at least one preaspirating orifice in the wall of the tool, and a plastic sleeve concentrically spaced about the tool for admitting fluid from a supply into the space between the tool and passing substantially all of the fluid through the preaspirating orifice.

In the application of ultrasonics to liposuction, instruments of varying configurations recently have been proposed. In U.S. Pat. No. 5,236,414, issued Aug. 17, 1993 to Katsuya-Takasu, a tubular body defining a suction passage has an opening in its front lower end, and an outer tube having a corresponding opening, by means of which fat tissue is crushed and/or emulsified due to the vibration of the front end of the tubular body and is then aspirated. In U.S. Pat. No. 5,514,086, issued May 7, 1996, to Parisi et al., an ultrasonically vibrated hollow probe has a port in its surface for aspiration and a tip substantially formed of plastic.

While the use of ultrasound has proven effective, its use must be carefully controlled. For example, external ultrasonic power is often used in order to ease the internal lipoplasty operation by breaking down the membranes of fat cells. A surgeon performing such a procedure has no feedback on how much energy is delivered over any given time span within a given area of treatment. Ultrasonic cutting and fragmentation tools suffer from the same limitation. Because of the importance of ultrasound treatments, a need exists for a method of measuring and controlling the energy delivered during the ultrasound treatment.

SUMMARY

A method and apparatus are provided for applying an ultrasound treatment to a portion of a human body. The method includes the steps of determining a temperature rise which the body portion will experience when a dosage limit of the ultrasound treatment has been reached. The method further includes the steps of disposing on the body portion an indicator adapted to provide a visual change at the determined temperature and applying ultrasound to the body portion until the indicator provides the visual change at the determined temperature.

DETAILED DESCRIPTION OF AN ILLUSTRATED EMBODIMENT

Figure 1:
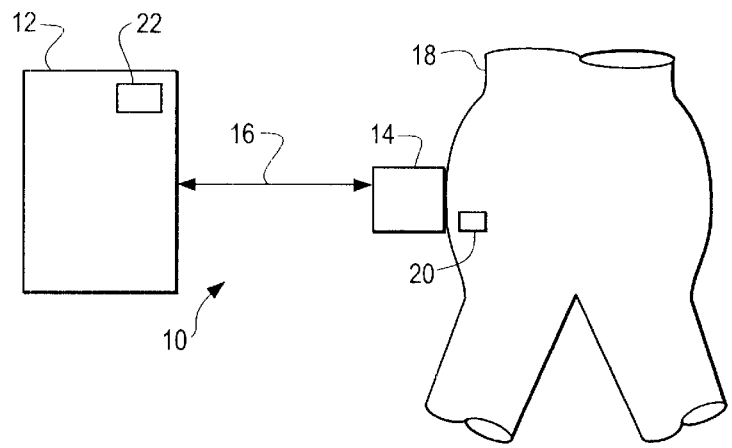
FIG. 1 depicts a system for applying ultrasound in accordance with an embodiment of the invention.

FIG. 1 depicts an ultrasonic system 10, generally, in accordance with an illustrated embodiment of the invention. The ultrasonic system 10 generally includes an ultrasonic power source 12, a transducer 14, a connector cable 16 and one or more thermal detectors 20.

Under the illustrated embodiment, an ultrasonic source (e.g., a generator) 12 generates a controlling electrical signal which is applied, through an attachment cable 16 to an ultrasonic transducer 14. The transducer 14 converts the electric signal into an ultrasound signal, which may then propagate into a portion 18 of a living human body.

The ultrasonic transducer 14 may be mechanically coupled to a probe for ultrasonic cutting or liposuction. In the alternative, the transducer 14 may also be an ultrasonic transceiver used for imaging.

Under the illustrated embodiment, the application of ultrasonic energy to the portion 18 is accompanied by the user of thermal indicators 20. The thermal indicators 20 may be attached to an outer surface of the portion 18 and may be used to detect a localized temperature of the portion 18. The detection of the localized temperature has been found to be important in avoiding overuse of ultrasonic energy. Such detection has important implications for both therapeutic and diagnostic ultrasound procedures.

The thermal indicators 20 may be a thermally reactive film (e.g., a thermochromatic film) fabricated to change color or opacity at a predetermined temperature. Such devices are well known and will not be discussed further, other than to note that the thermal indicators 20 differ from prior art devices (i.e., used with the human body) in that the indicators 20, are generally fabricated to provide a response only at a predetermined temperature above a normal body temperature.

The thermal indicators 20 may be fabricated of a thin plastic sandwich with a colored background layer which may be revealed only when the temperature of the portion 18 exceeds the calibrated temperature of the indicator 20. Further, alpha-numeric coding (e.g., "DOSAGE REACHED") may be printed on the background and may only be revealed when the portion 18 exceeds the calibrated temperature of the indicator 20.

The indicators 20 may be fabricated with an adhesive disposed on a rear surface, which allows the indicator 20 to be directly attached to the skin of a patient at nearly any location. The relatively thin nature of the indicator 20 allows the transducer 14 to be swept over the indicator 20 without interaction with the ultrasonic signal or interference with transmission of the ultrasonic signal into the portion 18.

Figure 3:
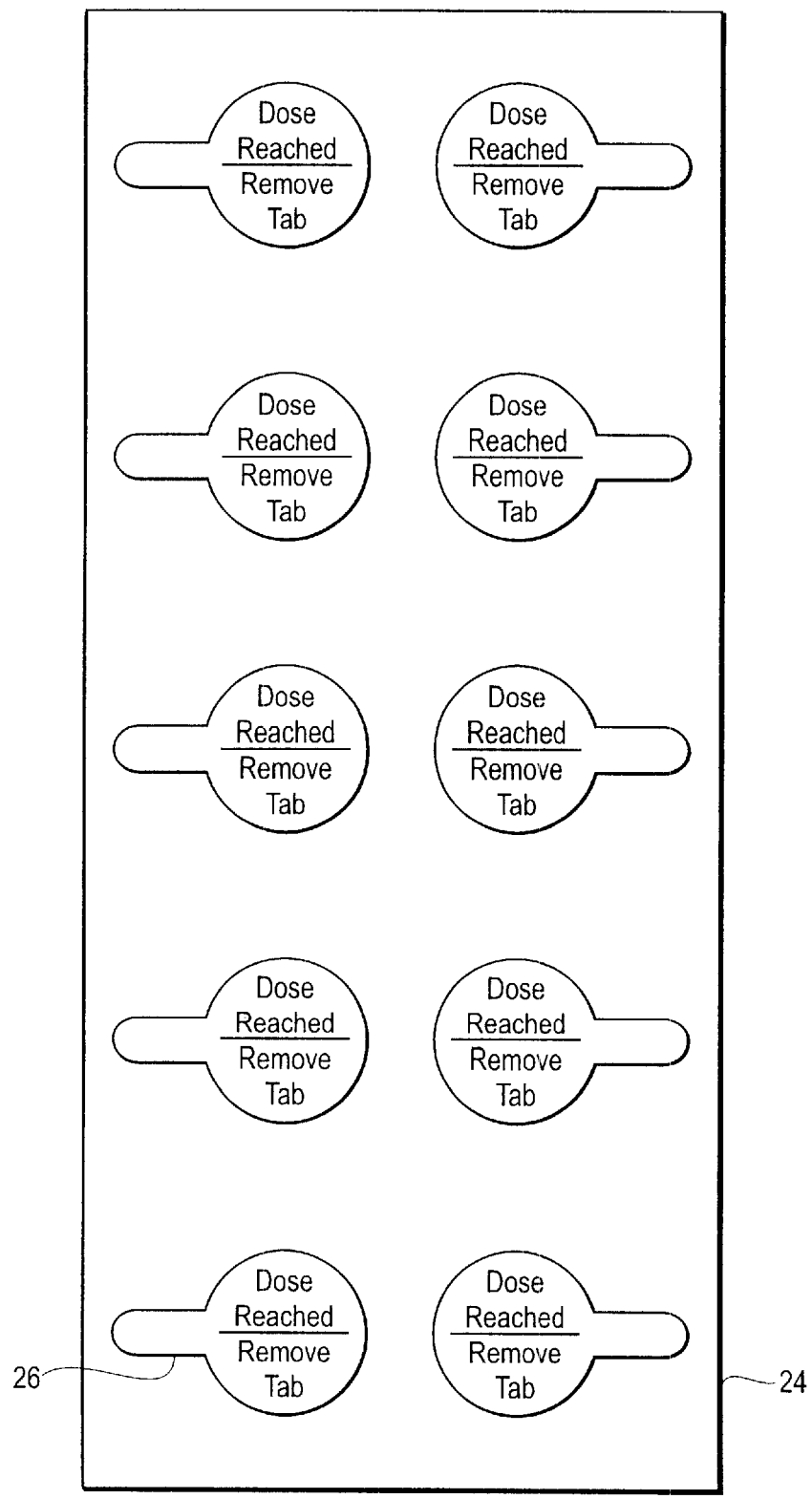
FIG. 3 depicts temperature indicators that may be used by the system of FIG. 1.

The indicators 20 may be provided to a user on a plastic backing 24 (FIG. 3). A temperature calibration level of each indicator 20 may be color-coded onto a tab 26 of the indicators 20.

The indicators 20 may be disposable and may be provided in packs of 10 each, as shown in FIG. 3. Such packs may be conveniently attached to an outside surface of the generator 12.

In use, the indicators 20 may be applied to the portion 18, as necessary. As dosage limits are reached (as noted by color change), the indicators 20 may be removed. A technician may then only focus on those areas of the portion 18 still containing indicators 20.

Figure 2:
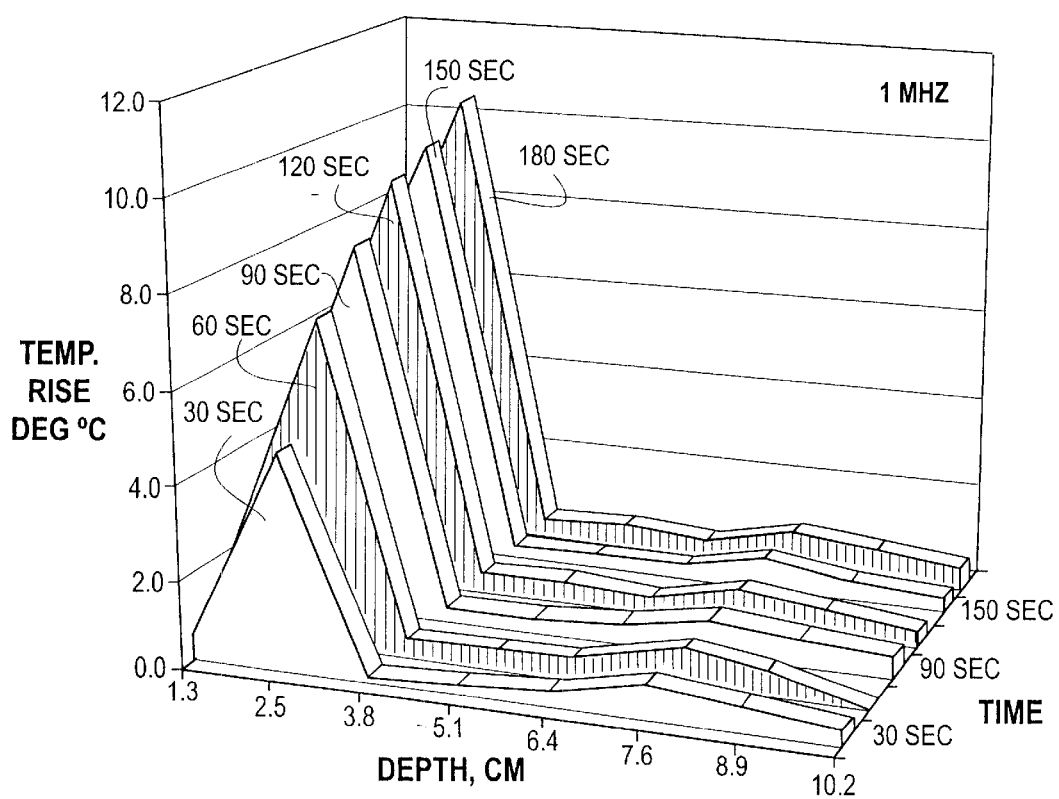
FIG. 2 is a graph of the heating effects of ultrasound that may be used with the system of FIG. 1.

FIG. 2 is an example of an in-depth heat distribution plot that may be obtained using the system 10 of FIG. 1 operating at a particular ultrasound frequency. More specifically, FIG. 2 is a graph of tissue temperature (versus depth and time) of the portion 18 where the transducer 14 is operated at 1.0 MHz and a power level of approximately 3 Joules/cm$^2$.

It may be noted from FIG. 2, that the 1.0 MHz signal has an ultrasound penetration depth which results in a tissue temperature rise at a depth of approximately 2.5 cm. Heating produced at other depths may be obtained by using slightly different ultrasonic frequencies. It has been found that an ultrasonic dosage limit of the portion 18 can be correlated to an ultrasound penetration depth, a mass and thickness of the treated layer and to a surface temperature overlying the treated areas.

For instance, the ultrasound energy heats up the inner layers of tissue at the ultrasound penetration depth. These layers radiate heat to the neighboring layers. In the case of abdominal lipoplasty (where the patient lays on her back), the temperature gradient is directed upwards because of the added convective effect. The convective effect causes the superficial layer and surface to be heated up. The surface temperature has been found to represent the inner temperature rise indirectly.

To practice the procedure, a mass of a fat layer may be determined for a particular area to be treated. An ultrasound penetration depth may be selected using a frequency control 22 on the source 12 based upon the thickness and mass to be treated. Using a specific heat of the area and power output of the transducer 14, a rate of rise of temperature may be determined for a particular dosage limit. By knowing a distance from the surface where heat localization will occur, a predicted temperature at the surface may be determined for the dosage limit.

It has been found that uniformity of ultrasonic dosage level in Joules/cm$^3$ can be achieved by the expeditious use of the indicators 20. For example, in the case of pretreatment for liposuction (i.e., to facilitate fat dissociation) it has been found that indicators calibrated to 1° C. above a normal body temperature works well for detecting (and limiting) ultrasound dosage for layers of fat of an intermediate thickness (e.g., one inch). A higher calibration temperature (e.g., 1.25–1.5b ° C.) may be used for thicker layers. A lower level (e.g., 0.25° C.) may be used for thinner layers.

In the case where the portion 18 of FIG. 1 is the pelvis of a human subject undergoing liposuction, a profile may be obtained of a fat depth to be removed. The treatment may be tailored to the specific location on the exterior surface of the portion 18.

Since a fat layer in a pelvic area of a human subject varies by location (e.g., across the buttocks), the dosage level may also vary, as may the ultrasonic frequency. Further, the presence of bone in an area of an ultrasonic treatment may reflect ultrasonic energy and provide a different temperature gradient across the fat layer.

To provide a measure of dosage, one or more temperature indicators 20 may be placed in the treatment area. The indicators 20 may be calibrated to a single temperature or a number of different indicators 20 may be used with each calibrated to a different temperature.

For example, for areas of intermediate fat thickness, an indicator 20 may be provided with a calibrated temperature value of 38° C. (e.g., 1° C. above a normal body temperature). Areas of thicker fat may be provided with a higher calibrated value (e.g., 39° C.).

Areas of less fat may be provided with a lower calibrated value (e.g., 37.25° C.).

In the case of pretreatment for liposuction, fat cell dissociation may be accomplished by first placing one or more indicators 20 over the area to be treated.

Following tumescent infusion, grid lines may be drawn on the patient, corresponding to the contour lines that may already have been drawn on the patient by the surgeon. The indicators 20 may be removed from a sterile pouch and individually placed at the centers of each of the grids. As the nurse moves the ultrasound applicator 14 over the grid, the indicators 20 will change color, upon reaching the appropriate temperature, and revealing the words "DOSE REACHED—REMOVE TAB". As the nurse removes each indicator and moves on to the next grid, the entire region maybe optimally dosed.

As an alternative to treating the grid spaces individually, the nurse may sweep the transducer 14 over the entire area to be treated. Where the areas treated include a continuum of thick and thin areas of fat, it would be expected that some indicators 20 would give indication of completion of treatment before other indicators 20. In this case, the technician would continue to treat the areas of thicker fat until the indicators 20 associated with those areas also give indication of completion of treatment.

A specific embodiment of a method and apparatus -for applying according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. Apparatus for applying an ultrasound treatment to a portion of a human body, such apparatus comprising:

means for applying ultrasound energy for the ultrasound treatment to the portion;

means adapted to be disposed on the portion for providing a color change only at a predetermined temperature when a dosage limit of the ultrasound treatment has been reached; and means adapted to secure the means for indicating to the portion of the human body.

2. The apparatus for applying an ultrasound,treatment as in claim 1 further comprising an ultrasonic source.

3. The apparatus for applying an ultrasound treatment as in claim 1 further comprising an ultrasonic transducer coupled to the ultrasonic source.

4. Apparatus for applying an ultrasound treatment to a portion of a human body, such apparatus comprising:

an ultrasound transducer adapted to apply the ultrasound treatment to the portion of the human body;

a thermochromatic strip adapted to be disposed on the portion and adapted to reveal a dosage reached message only at a predetermined temperature when a dosage limit of the ultrasound treatment has been reached; and means adapted to secure the thermochromatic strip to the portion of the human body.

5. The apparatus for applying an ultrasound treatment as in claim 4 wherein the means for securing further comprise and adhesive disposed on a surface of the thermochromatic strip.

6. The apparatus for applying an ultrasound treatment as in claim 4 further comprising an ultrasonic source.

7. The apparatus for applying an ultrasound treatment as in claim 4 further comprising an ultrasonic transducer coupled to the ultrasonic source.

8. The apparatus for applying an ultrasound treatment as in claim 4 wherein the thermochromatic strip further comprises a tab color-coded with the predetermined temperature.

9. A method of applying an ultrasound treatment to a portion of a human body, such method comprising the steps of:
   determining a temperature rise which the body portion will experience when a dosage limit of the ultrasound treatment has been reached;
   disposing on a surface of the body portion an indicator adapted to provide a visual change only at the determined temperature;
   applying ultrasound to the body portion until the indicator provides the visual change at the determined temperature.

10. The method of determining when a dosage limit has been reached as in claim 9 wherein the step of determining a temperature rise further comprises determining an ultrasound penetration depth to be achieved for the body portion.

11. The method of determining when a dosage limit has been reached as in claim 9 wherein the step of determining an ultrasound penetration depth to be achieved for the body portion further comprises selecting a frequency of the ultrasound source to achieve the ultrasound penetration depth.

12. The method of determining when a dosage limit has been reached as in claim 8 wherein the step of selecting a frequency of the ultrasound heating source further comprises determining an average depth of penetration of the ultrasound for the selected frequency.

13. Apparatus for applying an ultrasound treatment to a portion of a human body, such apparatus comprising:
   means adapted to be disposed on a surface of the portion for providing an opacity change only when a dosage limit of the ultrasound treatment has been reached;
   means for applying ultrasound to the body portion until the means for providing indicates that the dosage limit has been reached.

14. The apparatus for applying as in claim 13 wherein the means for applying ultrasound further comprises means for controlling an ultrasound penetration depth to be achieved for the body portion.

15. The apparatus for applying as in claim 13 wherein the means for providing the opacity change further comprises a thermochromatic strip.

16. The apparatus for applying as in claim 15 wherein the thermochromatic strip further comprises a relatively thin plastic sandwich.

17. The apparatus for applying as in claim 16 wherein the plastic sandwich further comprises a colored background.

18. The apparatus for applying as in claim 17 wherein the colored background further comprises alpha-numeric characters.

* * * * *